United States Patent [19]

Kakimoto et al.

[11] Patent Number: 4,985,245
[45] Date of Patent: Jan. 15, 1991

[54] TPA-CONTAINING MEDICAL COMPOSITION

[75] Inventors: Fumio Kakimoto; Naoki Asakawa; Yasuo Ishibashi, all of Gifu; Yasuo Miyake, Aichi, all of Japan

[73] Assignee: Eisai Co., Ltd., Tokyo, Japan

[21] Appl. No.: 430,949

[22] Filed: Nov. 3, 1989

Related U.S. Application Data

[63] Continuation of Ser. No. 32,585, Apr. 1, 1987, abandoned.

[30] Foreign Application Priority Data

Apr. 2, 1986 [JP] Japan ................................. 61-74370

[51] Int. Cl.$^5$ .................... A61K 37/547; A61K 31/13
[52] U.S. Cl. ................................ 424/94.3; 424/94.64; 514/669; 514/822
[58] Field of Search ................... 424/4, 5, 94.3, 94.64, 424/94.63; 514/669, 822

[56] References Cited

U.S. PATENT DOCUMENTS 4,568,544 2/1986 Hasegawa et al. ................ 424/94.1
4,647,447 3/1987 Gries et al. ............................ 424/4

OTHER PUBLICATIONS

Verebely et al., cited in Chem. Abstracts 70: 113570z (1969).

Primary Examiner—Jacqueline Stone
Attorney, Agent, or Firm—Wenderoth, Lind & Ponack

[57] ABSTRACT

A medical composition which contains a tissue Plasminogen Activator (tPA) in combination with meglumine or a salt thereof.

6 Claims, No Drawings

TPA-CONTAINING MEDICAL COMPOSITION

This application is a continuation of now abandoned application, Ser. No. 07/032,585 filed on Apr. 1, 1987.

BACKGROUND OF THE INVENTION (1) Field of the Invention

This invention relates to a medical composition containing a tissue Plasminogen Activator (hereinafter called "tPA"). More specifically, the present invention relates to a tPA-containing medical composition with increased water-solubility of tPA, which comprises tPA in combination with meglumine or a salt thereof.

(2) Description of the Prior Art

It is known that tPA acts on plasminogen in a living body to form plasmin and this plasmin destroys fibrin networks of thrombi to dissolve the same, and tPA is hence a substance useful for the treatment of circulatory disorders caused by the formation of thrombi.

However, tPA is a protein having an extremely low solubility in water. It is therefore very difficult to formulate tPA into a preparation which is administered after its dissolution in water, for example, into an injection. This is the greatest obstacle for the utilization of tPA in actual therapy.

SUMMARY OF THE INVENTION

An object of this invention is therefore to provide a tPA-containing medical composition in which the water-solubility of tPA has been increased to a degree sufficient to permit the use of tPA in therapy.

The present inventors carried out a variety of investigations with a view toward developing a technique to increase the solubility of tPA in water. As a result, it was found that a composition with improved water-solubility of tPA can be obtained by incorporating a diisocyanate-bound partial hydrolyzate of gelatin or arginine. Applications for patents have already been filed on the basis of these findings (Japanese Pat. application Nos. 198,629/1985 and 258,624/1985).

The present inventors have proceeded with a further investigation. As a result, it has now been found that addition of meglumine or a salt thereof to tPA can significantly increase the solubility of tPA further in water, leading to completion of this invention.

In one aspect of this invention, there is thus provided a medical composition containing a tissue Plasminoqen Activator (tPA), which comprises tPA in combination with meqlumine or a salt thereof.

The solubility of tPA has been increased to a considerable extent bY the addition of meglumine or the salt thereof.

The above and other objects, features and advantages of the present invention will become apparent from the following description and the appended claims.

DETAILED DESCRIPTION OF THE INVENTION AND PREFERRED EMBODIMENTS

In the present invention, tPA may be that which is extracted from a natural source or that obtained from a microorganism prepared artificially by a bioengineering technique or a culture broth of animal cells. This invention is not limited to any specific origin for tPA.

Meglumine or a salt thereof is employed in this invention. Although meglumine available in a salt form may be used directly as the salt of meglumine, the salt of meglumine can be provided by incorporating both meglumine and an inorganic or organic acid in a composition of this invention. Illustrative examples of such a salt may include the hydrochloride, acetate, lactate, gluconate, etc.

The medical composition of the present invention includes not only a solid or aqueous composition in which tPA and meglumine or a salt thereof are contained in combination but also a composition in such a form that tPA and meglumine or a salt thereof are individually packed, such as a vial containing lyophilized tPA and an ampule containing an aqueous solution of meglumine or a salt thereof and adapted for the dissolution of the lyophilized tPA, like an injection which can be formulated prior to its use.

The composition of the present invention may further contain auxiliary ingredients routinely employed in the formulation of dosable medical preparations, for example, one or more fillers, stabilizers, buffers, isotonic agents, etc. as needed.

The production of the composition of this invention may be carried out by a usual production method for a desired preparation form. A preparation method will next be described by way of example. An aqueous tPA solution is filled in portions in vials and is then lyophilized, thereby providing vials enclosing tPA-containing powder. Separately, an aqueous solution of the additive according to this invention is filled in portions in vials. One of the former vials is combined with one of the latter vials to provide a composition of this invention.

It is an effect of this invention that the solubility of tPA in water has been increased, whereby a high-concentration aqueous solution of tPA has been provided. As a specific example, a tPA-containing injection having a high potency can be provided. According to experiments which will be described subsequently, the solubility of tPA in water was 2100 U/ml when meglumine was not added while the addition of meglumine increased it to 17,000 U/ml at 1%, 85,000 U/ml at 2% and 331,000 U/ml at 5% respectively, in which U (potency unit) means the solubility of tPA in water. Namely, significant effects of meglumine for the increase of the solubility of tPA in water are observed.

EXAMPLES

The present invention will be described more specifically by the following Examples.

EXAMPLE 1

An aqueous solution containing 10 g of meglumine and 3 g of mannitol was adjusted to pH 7 with hydrochloric acid. The total volume of the thus-adjusted solution was 100 ml. Ten million units of tPA were then added, whereby an aqueous solution containing 1,000,000 units of tPA was prepared under sterile conditions. One-ml portions of the aqueous solution were pipetted in vials, lyophilized and then sealed hermetically.

Separately, ampules each containing 2 ml of distilled water for injection were prepared for dissolution.

EXAMPLE 2

Ten million units of tPA powder, which had been prepared under sterile conditions, and 3 g of sterile mannitol were mixed uniformly. In vials, the resultant mixture was filled and hermetically sealed in portions so that tPA was contained in an amount of 100,000 units per vial.

Separately, an aqueous solution containing 10 g of meglumine was adjusted to pH 7 with lactic acid under sterile conditions. The total volume of the thus-adjusted aqueous solution was 200 ml. Ampules each containing 2 ml of the resultant aqueous solution were prepared for dissolution.

Advantages of this invention will next be described by the following Experiments.

EXPERIMENT 1 tPA samples in an amount equivalent to 400,000 units were weighed separately in small test tubes, to which there were respectively added 1 ml of aqueous solutions containing meglumine and adjusted to pH 7 respectively with various acids in an amount equivalent to the meglumine. After stirring, the resultant mixtures were separately centrifuged to obtain supernatants as samples. Incidentally, the concentration of meglumine in each sample was 2%. In addition, aqueous solutions were prepared in exactly the same manner as the test samples except that in place of meglumine, sodium hydroxide was used in a molar amount equal to the meglumine, thereby providing comparative samples.

A predetermined amount of each sample was taken out and diluted with 0.1M tris-HCl buffer (pH 8; BSA was contained), followed by measurement of tPA activity (U/ml) by a fibrin plate.

Results are summarized in Table 1. Numerical values given in Table 1 indicate tPA activities (U/ml). From Table 1, it is apparent that the solubility of tPA is increased by addition of a suitably-selected acid and is increased further to a significant extent by addition of meglumine.

TABLE 1

| Kind of acid | Test sample | Comparative sample |
| --- | --- | --- |
| Acetic acid | 62,000 | 740 |
| Lactic acid | 82,000 | 16,800 |
| Gluconic acid | 79,000 | 46,100 |
| Hydrochloric acid | 85,000 | 9,000 |

EXPERIMENT 2

Test samples were provided in the same manner as in Example 1 except that the concentration of meglumine was 1%, 2% and 5% and hydrochloric acid was employed singly as an acid, followed by measurement of their tPA activities (U/ml). Results are shown in Table 2. It is understood that the solubility of tPA increases as the concentration of meglumine increases.

TABLE 2

| Meglumine concentration (%) | tPA activities (U/ml) |
| --- | --- |
| 1 | 17,000 |
| 2 | 85,000 |
| 5 | 331,000 |

Having now fully described the invention, it will be apparent to one of ordinary skill in the art that many changes and modifications can be made thereto without departing from the spirit or scope of the invention as set forth herein.

We claim:

1. A medical composition containing a tissue Plasminogen Activator (tPA, which comprises tPA and meglumine or a salt thereof.

2. The medical composition as claimed in claim 1, wherein meglumine is contained in a form of a salt selected from the group consisting of meglumine hydrochloride, acetate, lactate and gluconate.

3. The medical composition as claimed in claim 2, wherein the salt has been formed by incorporating meglumine and the corresponding inorganic or organic acid in the composition.

4. The medical composition as claimed in claim 1, wherein tPA and meglumine or the salt thereof are contained in separate packages of the same set.

5. The medical composition as claimed in claim 4, wherein the meglumine or the salt thereof is in the form of an aqueous solution thereof.

6. The medical composition as claimed in claim 1, further comprising mannitol.

* * * * *